United States Patent
Hirano et al.

(10) Patent No.: US 9,222,920 B2
(45) Date of Patent: Dec. 29, 2015

(54) ELEMENTAL ANALYZER

(71) Applicant: Horiba, Ltd., Kyoto (JP)

(72) Inventors: Akihiro Hirano, Kyoto (JP); Takahiro Yamada, Kyoto (JP)

(73) Assignee: HORIBA, LTD. (JP)

( * ) Notice: Subject to any disclaimer, the term of this patent is extended or adjusted under 35 U.S.C. 154(b) by 310 days.

(21) Appl. No.: 13/758,478

(22) Filed: Feb. 4, 2013

(65) Prior Publication Data

US 2013/0199268 A1  Aug. 8, 2013

(30) Foreign Application Priority Data

Feb. 3, 2012 (JP) .................................. 2012-021757

(51) Int. Cl.
    G01N 33/20 (2006.01)
    G01N 30/00 (2006.01)
    G01N 1/40 (2006.01)
    G01N 33/38 (2006.01)

(52) U.S. Cl.
    CPC .......... *G01N 30/0005* (2013.01); *G01N 1/4022* (2013.01); *G01N 33/203* (2013.01); *G01N 33/388* (2013.01)

(58) Field of Classification Search
    CPC ..... G01N 33/203; G01N 31/12; G01N 30/66; G01N 33/20; G01N 33/206
    See application file for complete search history.

(56) References Cited

U.S. PATENT DOCUMENTS 3,065,060 A * 11/1962 Roehrig et al. .................. 422/89
3,293,902 A * 12/1966 Kraus .......................... 73/19.07
3,407,041 A * 10/1968 Kraus ............................. 436/75
3,949,590 A *  4/1976 Boillot ......................... 73/19.07
3,985,505 A * 10/1976 Bredeweg ..................... 436/160
4,018,418 A *  4/1977 Dion-Biro .................... 251/63.6
4,248,598 A *  2/1981 Blunck ......................... 436/146
4,305,906 A * 12/1981 Mikasa et al. ................. 422/62

(Continued)

FOREIGN PATENT DOCUMENTS

JP     62093629 A    4/1987
JP   2001099825 A    4/2001

(Continued)

OTHER PUBLICATIONS

Machine Translation of JP 2008-064460 A which was originally published on Mar. 21, 2008.*

(Continued)

*Primary Examiner* — David A Rogers
(74) *Attorney, Agent, or Firm* — Cantor Colburn LLP

(57) ABSTRACT

In order to provide an elemental analyzer that, without providing a buffer tank, can cope with measurements of a low concentration sample to a high concentration sample on the basis of a simple configuration, the elemental analyzer is provided with: an extraction furnace 1 adapted to heat a sample contained in a crucible R, and gasify an element contained in the sample into sample gas; an introduction flow path L1 adapted to introduce carrier gas into the extraction furnace 1; a lead-out flow path L2 adapted to, from the extraction furnace, lead out mixed gas in which the sample gas and the carrier gas are mixed; an elemental analysis part 3 that is provided in the lead-out flow path L2 and analyzes elements contained in the mixed gas; a bypass flow path L3 that branches from the introduction flow path L1 and joins the lead-out flow path L2; and a valve 4 that is provided in the bypass flow path L3 and can adjust an opening level.

4 Claims, 4 Drawing Sheets

(56) References Cited

U.S. PATENT DOCUMENTS

| | | | |
|---|---|---|---|
| 4,332,591 A * | 6/1982 | Oi et al. | 436/114 |
| 4,525,328 A * | 6/1985 | Bredeweg | 422/80 |
| 4,582,686 A * | 4/1986 | Tsuji | 422/80 |
| 4,711,854 A * | 12/1987 | Pregnall et al. | 436/144 |
| 5,522,915 A * | 6/1996 | Ono et al. | 75/385 |
| 5,612,225 A * | 3/1997 | Baccanti et al. | 436/114 |
| 6,627,155 B1 * | 9/2003 | Uemura et al. | 422/83 |
| 6,827,903 B2 * | 12/2004 | Guerra | 422/83 |
| 2002/0112658 A1 * | 8/2002 | Holder et al. | 117/15 |
| 2009/0121129 A1 * | 5/2009 | Wang et al. | 250/287 |
| 2012/0103062 A1 * | 5/2012 | Hsiao et al. | 73/23.37 |
| 2013/0316465 A1 * | 11/2013 | Steude et al. | 436/160 |

FOREIGN PATENT DOCUMENTS

| | | |
|---|---|---|
| JP | 2001356120 A | 12/2001 |
| JP | 2002202300 A | 7/2002 |
| JP | 2004093310 A | 3/2004 |
| JP | 2006506640 A | 2/2006 |
| JP | 2008064460 A | 3/2008 |
| JP | 201032264 A | 2/2010 |
| WO | 2004046517 A | 6/2004 |

OTHER PUBLICATIONS

Official English-language translation of JP 2008-064460A which was originally published on Mar. 21, 2008.*

Japanese Office Action for Application: 2012021757, dated Nov. 26, 2013, with Partial English Translation.

* cited by examiner

ELEMENTAL ANALYZER

Priority under 35 U.S.C. §119(a) is claimed from Japanese Application No. 2012-021757, filed 3 Feb. 2012, the disclosure of which is also incorporated herein by reference.

TECHNICAL FIELD

The present invention relates to an elemental analyzer for analyzing elements such as nitrogen (N), hydrogen (H), and oxygen (O) contained in a sample such as iron, non-ferrous metal, or ceramics.

BACKGROUND ART

As this sort of elemental analyzer, there is one that holds a graphite crucible, which contains a sample, between a pair of electrodes in an extraction furnace; directly applies voltage to the crucible to thereby heat the crucible and the sample inside the crucible; and analyzes sample gas generated by the heating to analyze elements contained in the sample.

More specifically, the above-described elemental analyzer is configured such that the extraction furnace is connected with an introduction flow path for introducing carrier gas having a constant flow rate, and mixed gas of the sample gas generated in the extraction furnace and the carrier gas can be led out from inside the extraction furnace to a lead-out flow path. Further, in an elemental analysis part provided in the lead-out flow path, concentration measurements of carbon monoxide (CO) and nitrogen ($N_2$) contained in the mixed gas are made to thereby analyze what elements are contained in the sample (see Patent Literature 1).

Meanwhile, in the case of a high concentration sample such as oxide or nitride, when heating is performed in the extraction furnace, a large amount of carbon monoxide (CO) or nitrogen ($N_2$) is generated as compared with other materials. As a result, the carrier gas is introduced into the extraction furnace at the constant flow rate, and therefore a concentration measured in each detection part exhibits a high concentration peak within a short time as indicated by a dashed line in a graph of FIG. 4.

That is, in the case of making an elemental analysis of the high concentration sample, as both of a CO detector and an $N_2$ detector used in the elemental analysis part, ones that can cope with high concentration measurements should be selected; however, on the other hand, the detectors that can be make the high concentration measurements tend to have lower sensor sensitivity. Accordingly, as indicated by the dashed line in FIG. 4, in the case where a detection time is short and the peak-like concentration change occurs, it is difficult to make the concentration measurements with accuracy.

In response to such a problem, there is an elemental analyzer 100 that is configured to increase measurement accuracy by, as illustrated in a schematic diagram of FIG. 3, in the lead-out flow path L2, providing a buffer tank B in a stage prior to the elemental analysis part 3 to blunt a profile of the concentration of the sample gas contained in the mixed gas and also increase the detection time in the elemental analysis part 3 as indicated by a solid line in FIG. 4.

However, in the case of providing the buffer tank B as described, corresponding capacity should be ensured inside a housing of the elemental analyzer 100, and therefore there arises a problem of increasing in size of the analyzer. Although the presence of the buffer tank B enables the elemental analysis of the high concentration sample to be made with accuracy, in the case of a low concentration sample, the presence of the buffer tank B prevents the detection because a concentration peak is made too low, or for another reason. That is, the above-described elemental analyzer 100 becomes an elemental analyzer specialized in high concentration samples, and therefore in the case of desiring to analyze a low concentration sample, another elemental analyzer should be prepared.

CITATION LIST

Patent Literature

Patent Literature 1: JPA 2010-32264

SUMMARY OF INVENTION

Technical Problem

The present invention is made in consideration of the problems as described above, and provides an elemental analyzer that can cope with measurements of a low concentration sample to a high concentration sample on the basis of a simple configuration without providing a buffer tank.

Solution to Problem

That is, the elemental analyzer of the present invention is provided with: an extraction furnace adapted to heat a sample contained in a crucible, and gasify an element contained in the sample into sample gas; an introduction flow path adapted to introduce carrier gas into the extraction furnace; a lead-out flow path adapted to lead out mixed gas from the extraction furnace, the mixed gas is that the sample gas and the carrier gas are mixed in; an elemental analysis part that is provided in the lead-out flow path and analyzes elements contained in the mixed gas; a bypass flow path that branches from the introduction flow path and joins the lead-out flow path; and a valve that is provided in the bypass flow path and whose opening level is adjustable.

If so, by appropriately adjusting the opening level of the valve, the carrier gas flowing through the introduction flow path can be distributed to the extraction furnace and the bypass flow path respectively at desired flow rates, and therefore a concentration of the sample gas in the mixed gas in the lead-out flow path can be controlled in a desired mode.

To describe more specifically, by decreasing a flow rate of the carrier gas flowing into the extraction furnace, an amount of the sample gas that is generated in the extraction furnace and flowed out toward the lead-out flow path per unit time can be decreased. Accordingly, even in the case where the sample is a high concentration sample, the sample gas is not entirely led out toward the lead-out flow path at once but can be led out toward the lead-out flow path little by little with taking time. As described, while leading out the sample gas little by little, the mixed gas is further diluted by the carrier gas separated toward the bypass flow path, and therefore a peak height of the concentration of the sample gas in the mixed gas, which is detected in the elemental analysis part, can be reduced. That is, the peak height of the concentration of the detected sample gas can be reduced, and in addition, a detection time can also be increased, so that substantially the same effect as that in the case of providing the buffer tank can be obtained. Accordingly even for a high concentration sample, an accurate elemental analysis can be made.

Further, in the case where the sample is a low concentration sample, for example, by decreasing the opening level of the valve, the flow rate of the carrier gas introduced into the extraction furnace can be increased to thereby perform control so as to achieve a concentration peak height and detection time suitable for the measurement.

From this, the elemental analyzer of the present invention can cope with all elemental analyses of a low concentration sample to a high concentration sample.

In order to be able to make an elemental analysis with accuracy depending on a sample, it is only necessary that the opening level of the valve is adjusted such that a concentration of the sample gas in the mixed gas in the elemental analysis part becomes equal to a predetermined concentration.

Configurations of the elemental analyzer particularly suitable for the case where the sample is a high concentration sample include one in which the opening level of the valve is adjusted such that a first flow rate has a smaller value than a second flow rate, wherein the first flow rate is a flow rate of carrier gas separated toward the extraction furnace from the carrier gas flowing through the introduction flow path, and the second flow rate is a flow rate of carrier gas separated toward the bypass flow path from the carrier gas flowing through the introduction flow path.

In order to be able to collect dust generated in the extraction furnace, and keep longer a configuration for collecting the dust, it is only necessary that a dust filter is further provided between the extraction furnace and the elemental analysis part in the lead-out flow path, and the bypass flow path is provided so as to join the lead-out flow path on a downstream side of the dust filter.

Advantageous Effects of Invention

As described, according to the elemental analyzer of the present invention, the bypass flow path that bypasses the extraction furnace and serves as a bypass between the introduction flow path and the lead-out flow path is provided, and also in the bypass flow path, the valve that can adjust the opening level is provided, so that by controlling a ratio between the flow rate of the carrier gas introduced into the extraction furnace and the flow rate of the carrier gas flowing through the bypass flow path, the concentration of the sample gas in the mixed gas in the lead-out flow path can be appropriately controlled. Accordingly, even in the case where the sample is a high concentration sample, the concentration and detection time of the sample gas in the mixed gas in the elemental analysis part can be adjusted to a concentration and length suitable for the measurement, respectively, and therefore the elemental analysis can be made with accuracy. Further, it is not necessary to provide a buffer tank for measuring the high concentration sample, and therefore an increase in size of the analyzer can be prevented. Still further, by changing the ratio in flow rate, the elemental analyzer can also cope with the case where the sample is a low concentration sample.

REFERENCE SIGNS LIST

Figure 1:
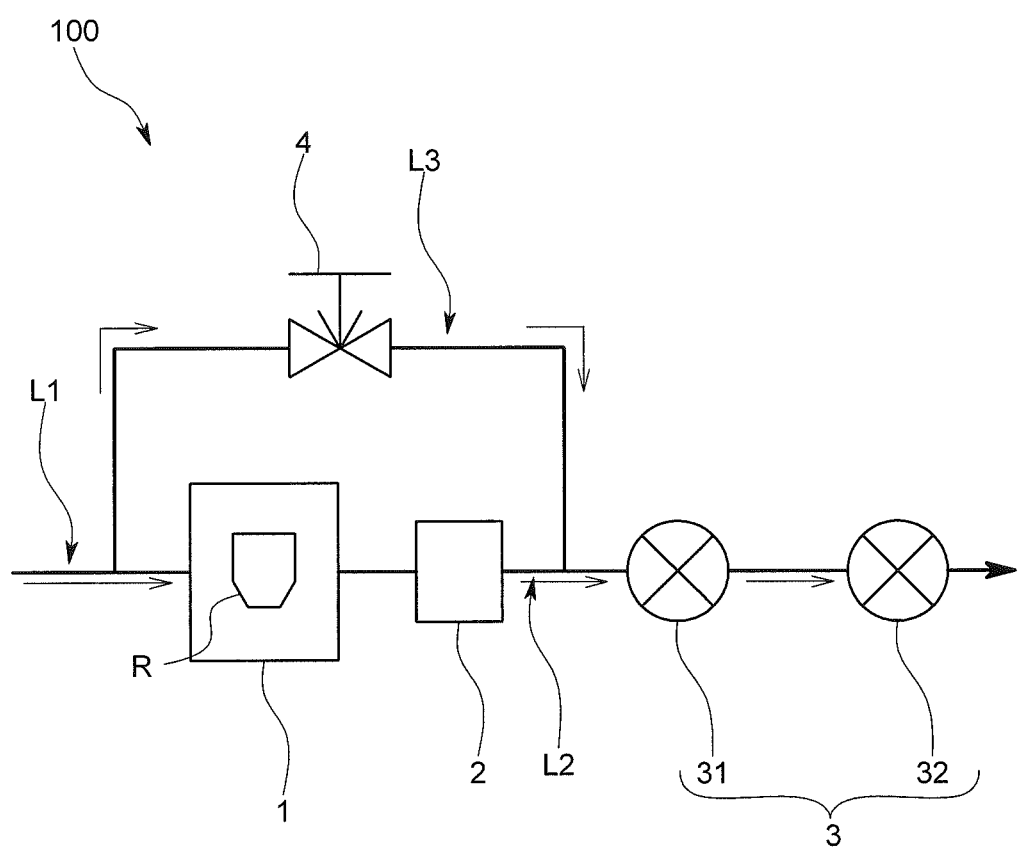
FIG. 1 is a schematic diagram illustrating a configuration of an elemental analyzer according to one embodiment of the present invention.

100 . . . Elemental analyzer
1 . . . Extraction furnace
3 . . . Elemental analysis part
4 . . . Valve
L1 . . . Introduction flow path
L2 . . . Lead-out flow path
L3 . . . Bypass flow path

DESCRIPTION OF EMBODIMENTS

An elemental analyzer 100 of the present invention is described referring to the drawings.

Configuration of Analyzer

The elemental analyzer 100 of the present embodiment is one that holds a graphite crucible R, which contains a sample, between a pair of electrodes in an extraction furnace 1; directly applies voltage to the crucible R to thereby heat the crucible R and the sample inside the crucible R; and uses sample gas generated by the heating to analyze elements contained in the sample.

Specifically, the elemental analyzer 100 is, as illustrated in FIG. 1, provided with: an introduction flow path L1 for introducing carrier gas such as He into the extraction furnace 1; and a lead-out flow path L2 for, from the extraction furnace 1, leading out mixed gas in which the sample gas and the carrier gas are mixed, in which in the lead-out flow path L2, at least a dust filter 2, and an elemental analysis part 3 that analyzes elements contained in the mixed gas are provided. Further, the elemental analyzer 100 of the present embodiment is one that is provided with: a bypass flow path L3 that branches from the introduction flow path L1 and joins the lead-out flow path L2; and a needle valve 4 that is provided in the bypass flow path 3 and can adjust an opening level.

The elemental analysis part 3 is configured to reduce the passing sample gas with, for example, an unillustrated platinum catalyst or the like, and then measure concentrations of respective gases with at least a CO detector 31 and an $N_2$ detector 32. The elemental analysis part 3 is one that, on the basis of results of the concentration measurements, analyzes amounts of oxygen and nitrogen contained in the original sample.

Analysis Settings and Operation

Settings and operation at the time of the analysis in the elemental analyzer 100 configured in the above manner are described. In the following description, the case where the carrier gas having a constant flow rate of 400 ml/min is introduced into the introduction flow path L1, and as the sample, a high concentration sample such as oxide or nitride is targeted is taken as an example to provide the description.

In the case of targeting the high concentration sample for the elemental analysis, the opening level of the valve 4 is adjusted such that a first flow rate, which is, of the carrier gas flowing through the introduction flow path L1, a flow rate of carrier gas separated toward the extraction furnace 1, has a smaller value than a second flow rate, which is, of the carrier gas flowing through the introduction flow path L1, a flow rate of carrier gas separated toward the bypass flow path L3. More specifically, the first flow rate is set to 100 ml/min and the second flow rate is set to 300 ml/min.

Figure 2:
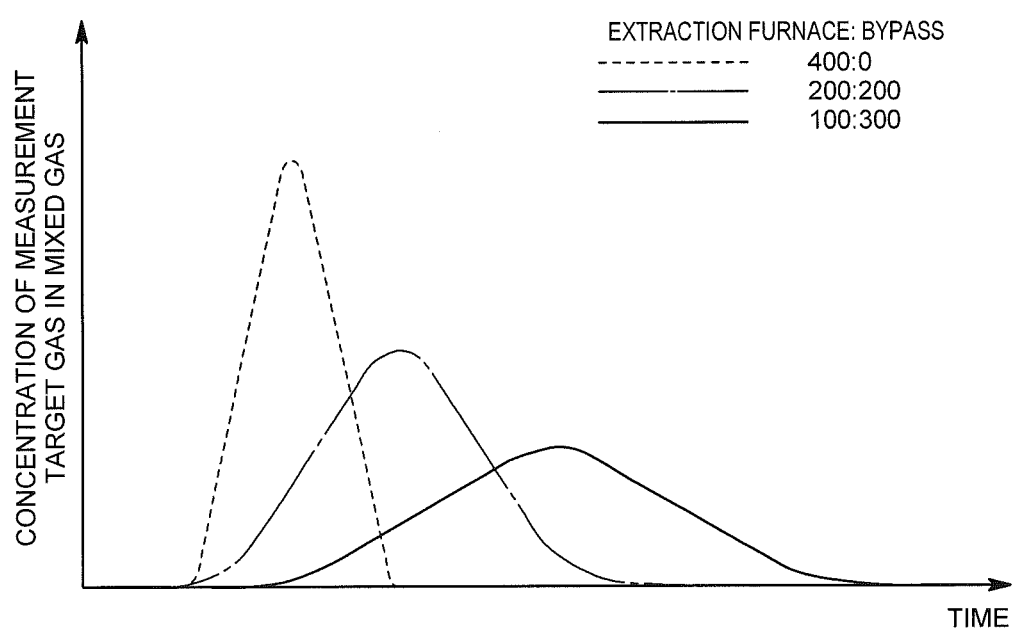
FIG. 2 is a schematic graph illustrating changes in measured concentration of sample gas in the case of changing a flow rate of carrier gas flowing through a bypass flow path in the same embodiment.
Figure 3:
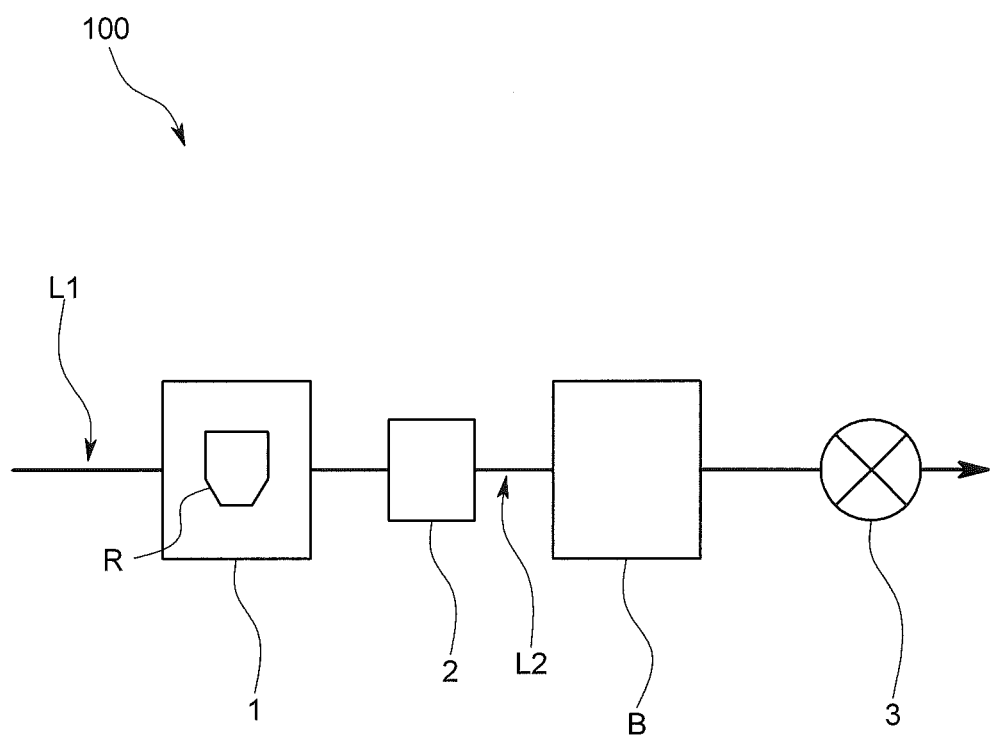
FIG. 3 is a schematic diagram illustrating a configuration of a conventional elemental analyzer.
Figure 4:
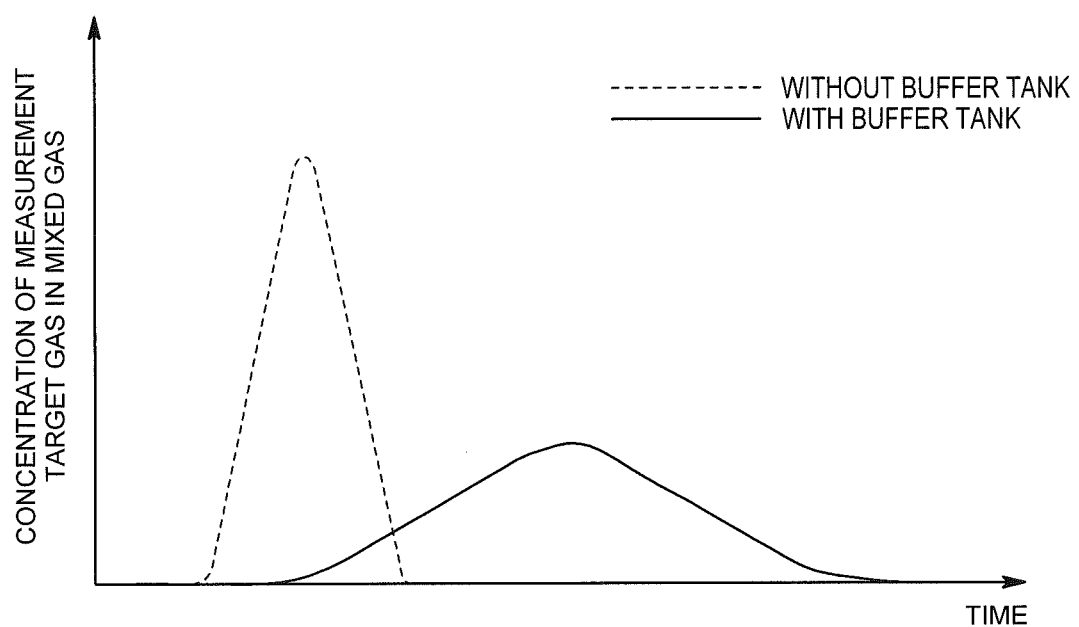
FIG. 4 is a schematic graph illustrating changes in measured concentration of sample gas measured in the case of making an elemental analysis of a high concentration sample in the conventional elemental analyzer.

If a flow separation ratio of the carrier gas is changed, the measurement result of the CO or $N_2$ concentration measured in the elemental analysis part 3 is changed as illustrated in a graph of FIG. 2. That is, in the case where the valve 4 is fully closed, and the whole of the carrier gas having the flow rate of 400 ml/min is introduced into the extraction furnace 1, the sample gas generated in the extraction furnace 1 is led out toward the lead-out flow path L2 at once, and therefore a measurement result exhibiting a high concentration and a narrow peak width is obtained as indicated by a dashed line. In such a state, it is necessary to use a detector for high concentration measurement, and also because of a short detection time, it is difficult to make an accurate elemental analysis in terms of sensor sensitivity.

On the other hand, in the case of separating a part of the carrier gas toward the bypass flow path L3, the flow rate of the carrier gas to be introduced into the extraction furnace 1 can be reduced, and therefore an amount of sample gas led out toward the lead-out flow path L2 per unit time can be reduced. Accordingly, by separating a predetermined amount of carrier gas toward the bypass flow path L3, as indicated by a long dashed short dashed line or a solid line, a profile of a measured concentration of measurement target gas can be blunted to reduce a peak height at the time of measurement and also increase a corresponding peak width. Consequently, even in the case of making an elemental analysis of a high concentration sample, without the necessity of using the detector that can measure high concentration, i.e., a detector having a wide measurement range, a detector having high sensor sensitivity can be used. Further, a detection time can be made longer, and therefore the elemental analysis can be made with accuracy.

Effect of the Present Embodiment

As described, according to the elemental analyzer 100 of the present embodiment, by adjusting the flow rate ratio between the carrier gas flowing into the extraction furnace 1 and the carrier gas flowing into the bypass flow path L3, a concentration of the sample gas in the mixed gas can be appropriately adjusted, and therefore the concentration can be set to a concentration suitable for characteristic of the sensors used in the elemental analysis part 3. Accordingly, not only for a high concentration sample but also for a low concentration sample, a similar adjustment can be made, and therefore for a wide variety of samples, the elemental analysis can be made only with the elemental analyzer 100 of the present embodiment.

Also, in the conventional case, in order to make an elemental analysis of a high concentration sample, it is necessary to provide the buffer tank in the lead-out flow path L2; however, in the present embodiment, only by adding a simple configuration having an extremely small capacity, i.e., the bypass flow path L3 and the valve 4, an equivalent effect can be obtained. Accordingly, while increasing the number of types of samples as analysis targets, an increase in size of the analyzer can be prevented.

Other embodiments are described.

In the above-described embodiment, elemental analyses of oxygen and nitrogen are made; however, the present invention may also make an elemental analysis of, for example, carbon or the like. In such a case, it is only necessary to provide a configuration necessary for the elemental analysis in the lead-out flow path.

What is provided in the bypass flow path is the needle valve; however, any valve is possible if the valve can appropriately adjust an opening level. Also, not the single body of valve, but a device including a flow rate control valve, such as a mass flow controller, may be provided in the bypass flow path. Further, a valve may be provided between a branch point between the introduction flow path and the bypass flow path and the extraction furnace. Even such a configuration can change the flow separation ratio of the carrier gas.

Besides, various modifications and combinations of the embodiments may be made without departing from the scope of the present invention.

INDUSTRIAL APPLICABILITY

According to the present invention, even in the case where the sample is a high concentration sample, a concentration and detection time of the sample gas in the mixed gas in the elemental analysis part can be adjusted to a concentration and length suitable for the measurement, respectively, and therefore the elemental analyzer that can analyze the elements with accuracy can be provided.

The invention claimed is:

1. An elemental analyzer comprising:
an extraction furnace adapted to heat a sample contained in a crucible, and gasify an element contained in the sample into sample gas;
an introduction flow path adapted to introduce carrier gas into the extraction furnace;
a lead-out flow path adapted to lead out mixed gas from the extraction furnace, the mixed gas is that the sample gas and the carrier gas are mixed in;
an elemental analysis part that is provided in the lead-out flow path and analyzes elements contained in the mixed gas;
a bypass flow path that branches from the introduction flow path and joins the lead-out flow path;
a valve that is provided in the bypass flow path and whose opening level is adjustable;
a dust filter between the extraction furnace and the elemental analysis part in the lead-out flow path; and
a junction that is provided between the dust filter and the elemental analysis part in the lead-out flow path, the junction being a merging point of the lead-out flow path and the bypass flow path, wherein
the bypass flow path is provided so as to join the lead-out flow path on a downstream side of the dust filter.

2. The elemental analyzer according to claim 1, wherein the opening level of the valve is adjusted such that a concentration of the sample gas in the mixed gas in the elemental analysis part becomes equal to a predetermined concentration.

3. The elemental analyzer according to claim 1, wherein the opening level of the valve is adjusted such that a first flow rate has a smaller value than a second flow rate, wherein
the first flow rate is a flow rate of carrier gas separated toward the extraction furnace from the carrier gas flowing through the introduction flow path, and
the second flow rate is a flow rate of carrier gas separated toward the bypass flow path from the carrier gas flowing through the introduction flow path.

4. The elemental analyzer according to claim 1, wherein,
the elemental analysis part includes multiple detectors that detect mutually different elements and are provided in series in the lead-out flow path, and
the junction is provided between the dust filter and a leading detector of the detectors.

* * * * *